United States Patent [19]

Ward

[11] Patent Number: 4,537,623

[45] Date of Patent: Aug. 27, 1985

[54] HERBICIDAL 2-(OXA OR THIA HETEROCYCLE)5-AMINO-3-OXO-4-(SUBSTITUTED-PHENYL)-2,3-DIHYDROFURANS

[75] Inventor: Carl E. Ward, San Jose, Calif.

[73] Assignee: Chevron Research Company, San Francisco, Calif.

[21] Appl. No.: 594,497

[22] Filed: Mar. 29, 1984

[51] Int. Cl.$^3$ .................. A01N 43/02; A01N 43/00; C07D 333/00

[52] U.S. Cl. .................. 71/90; 71/88; 549/13; 549/60; 549/414; 549/472

[58] Field of Search .................. 549/13, 14, 22, 60, 549/370, 377, 414, 448, 472; 71/88, 90

[56] References Cited

U.S. PATENT DOCUMENTS

| | | | |
|---|---|---|---|
| 4,169,202 | 9/1979 | Jirkousky et al. | 549/60 |
| 4,233,308 | 11/1980 | Kunz et al. | 549/60 |
| 4,407,817 | 10/1983 | Chan | 549/60 |
| 4,441,910 | 4/1984 | Shapiro | 71/90 |

FOREIGN PATENT DOCUMENTS

| | | |
|---|---|---|
| 42-19090 | 9/1967 | Japan . |
| 44-13710 | 6/1969 | Japan . |
| 1521092 | 3/1975 | United Kingdom . |
| 2080289 | 2/1982 | United Kingdom . |

OTHER PUBLICATIONS

Helvetica Chmica Acta–vol. 66, Fasc. 1 (1983)–Nr. 31.
Chem. Abstracts, vol. 70, 1969.
Heterocycles vol. 95, 1981.
Meier et al., Chem. Abst., vol. 94 (1981) 13818v.

*Primary Examiner*—Alan Siegel
*Attorney, Agent, or Firm*—J. A. Buchanan, Jr.; L. S. Squires

[57] ABSTRACT

Herbicidal 2-(oxaheterocycle or thiaheterocycle)-5-amino-3-oxo-4-(substituted-phenyl)-2,3-dihydrofurans and derivatives thereof. The compounds generally exhibit both pre-emergence and post-emergence phytotoxicity and are useful as herbicides and also plant growth regulating agents at low dosages.

35 Claims, No Drawings

HERBICIDAL 2-(OXA OR THIA HETEROCYCLE)5-AMINO-3-OXO-4-(SUBSTITUTED-PHENYL)-2,3-DIHYDROFURANS

BACKGROUND OF THE INVENTION

This invention relates to 2-(oxa and thia heterocycle) 5-amino-3-oxo-4-(substituted-phenyl)-2,3-dihydrofurans and derivatives thereof and to the use of such compounds as herbicides and plant growth regulators.

Chemiker-Zeitung 104 (1980) No. 10, Pages 302–303, is an academic paper disclosing the ring closure of 1-(dimethylamino)-2,4-diphenyl-1-buten-3,4-dione to yield 5-dimethylamino-2,4-diphenyl-2,3-dihydrofuran. British Pat. No. 1,521,092, discloses certain 3-phenyl-5-substituted-4(1H)-pyrid-ones or -thiones as herbicides. Japanese Patent Application No. 13,710/69 (Chemical Abstracts 71:61195e) discloses 5-amino-3-oxo-4-(phenyl or 4-chlorophenyl)-2,3-dihydrofurans. Japanese Patent No. 19090 (Chemical Abstracts 69P10352e) discloses certain 2,3-dihydrothiophenes as pharmaceuticals. *Helvetica Chemica Acta*, Volume 66, Pages 362–378 (1983) discloses 5-N-cyclopropyl-4-phenyl-2-methoxycarbonylmethylene-3-furanone as part of an academic chemical synthesis discussion.

In my copending application U.S. Ser. No. 505,169, filed June 17, 1983, I disclosed certain 2-aryl 5-amino-3-oxo-4-(substituted phenyl)-2,3-dihydrofuran derivatives and their use as herbicides.

SUMMARY OF THE INVENTION

The present invention provides compounds having both pre-emergence and post-emergence herbicidal activity and having especially good pre-emergence activity against a broad spectrum of both broad-leaf weeds and grassy weeds. At lower application rates the compounds also exhibit plant growth regulating properties.

The compounds of the present invention can be represented by the following formula:

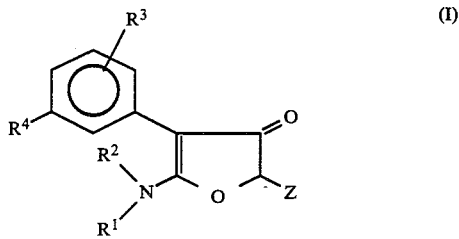

wherein $R^1$ and $R^2$ are independently hydrogen, lower alkyl, having 1 through 4 carbon atoms, or alkenyl having 3 through 6 carbon atoms;

$R^3$ is hydrogen, lower alkyl, lower alkoxy, halo, or trifluoromethyl; $R^4$ is lower alkyl, lower alkoxy, halo, or trifluoromethyl;

Z is a saturated or unsaturated heterocycle radical having five or six ring atoms including one or two oxygen or sulfur atoms and the remainder are carbon atoms. The invention also comprises compatible salts of the compound of Formula (I).

The compounds exist as keto-enol tautomer isomers with respect to the 3-keto group shown in Formula I. Also, where the compounds of Formula (I) have an asymmetric carbon atom they can exist as optical isomers. The above formula is intended to encompass both the respective tautomers and optical and geometric isomers where they exist as well as mixtures thereof and the respective isomers as well as mixtures thereof are encompassed within the invention.

It has also been discovered that the presence of a 3-trifluoromethyl substituent on the 4-phenyl group of the compounds of the present invention generally very substantially enhances herbicidal activity.

In a further aspect the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, which comprises treating the growth medium and/or the foliage of such vegetation with a herbicidally effective amount of the compound(s) of Formula (I) and/or compatible salts thereof.

In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 3–7 set forth hereinbelow on Pages 14–23. In terms of substituents, the preferred compounds are those wherein $R^1$ and $R^2$ are independently hydrogen, methyl, ethyl or n-propyl, and more preferably one of $R^1$ or $R^2$ is hydrogen and the other is hydrogen, methyl, ethyl or n-propyl, preferably methyl or ethyl. Preferably, $R^3$ is hydrogen and $R^4$ is trifluoromethyl or halo, especially trifluoromethyl. When $R^1$ and/or $R^2$ is alkenyl, preferably the alkenyl group has 3 or 4 carbon atoms.

The Z heterocycle group can be represented by the formulas:

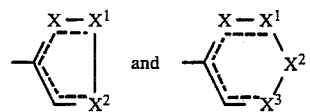

wherein one or two of X, $X^1$, $X^2$ or $X^3$ are independently sulfur (divalent sulfur) or oxygen and the remainder is carbon atoms and the inner ring dotted lines indicate that the ring can be saturated, unsaturated or partially saturated. The preferred Z heterocyclic groups are thiophene, furan, pyran and thiopyran.

The compounds of the invention wherein $R^1$ and $R^2$ are each hydrogen can be prepared by the following schematically represented process:

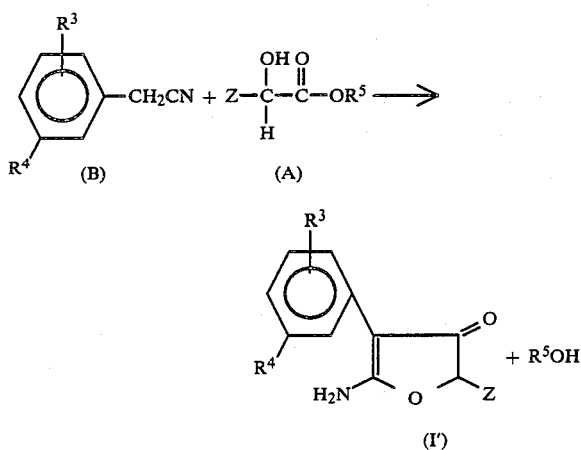

wherein $R^3$, $R^4$, and Z are as defined hereinabove; and $R^5$ is lower alkyl, aryl (e.g., phenyl) or arylalkylene (e.g., benzyl).

This process can be conveniently effected by contacting Compound (B) with Compound (A), and a strong base (e.g., sodium methoxide, sodium ethoxide), preferably in an inert organic solvent.

Typically, this process is conducted at temperatures in the range of about from 0° to 100° C., preferably 75° to 85° C. for about from 5 to 36 hours, preferably 18 to 24 hours, using about from 1 to 10, preferably 1 to 1.2 moles of Compound (A) per mole of Compound (B).

Suitable strong bases which can be used include, for example, alkali metal alkanolates, for example, sodium methoxide, sodium ethoxide, potassium ethoxide, sodium hydride, potassium hydride, and the like. The strong base should preferably be one which does not yield water as a by-product in this reaction system.

Suitable inert solvents which can be used include, for example, lower alkanols (for example, methanol, ethanol, and propanol) tetrahydrofuran, dimethoxyethane, dioxane, and the like, and compatible mixtures thereof. Conveniently, the alkali metal alkanolate is prepared in situ by reacting an alkali metal with excess alkanol which in turn serves as solvent for the above reaction.

The starting materials of Formula (B) are generally known materials and can be prepared by known procedures, or obvious modifications thereof (i.e., substitution of appropriate starting materials). The preparation of Compound (B) is for example described in Org. Syn. Coll., Volume 1, 107 (1941).

The hydroxy esters of Formula (A) are also generally known compounds and can be prepared by known procedures or by obvious modifications thereof (e.g., by using appropriately substituted starting materials). For example, via the reaction of the corresponding heterocycle-hydroxyacetonitrile with hydrogen chloride in methanol to yield the corresponding (2-imino-2-methoxy-1-hydroxyethyl)heterocycle hydrochloride salt which in turn can be hydrolyzed to the corresponding ester of formula A. The initial heterocycle-hydroxyacetonitrile starting material can be prepared via the reaction of the corresponding formyl heterocycle with sodium cyanide.

The compound of Formula (I) wherein one or both of $R^1$ and $R^2$ are lower alkyl or lower alkenyl can be prepared by alkylation (or alkenylation) of the amino group:

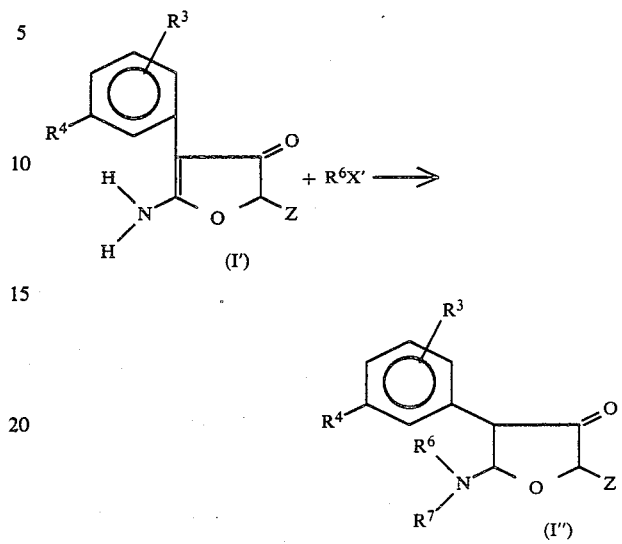

wherein $R^3$, $R^4$ and Z are as defined hereinabove; $R^6$ is lower alkyl or lower alkenyl; $R^7$ is hydrogen or $R^6$; and $R^6X'$ is an alkylation or alkenylation agent.

This process can be effected by contacting Compound (I') with a suitable alkylation or alkenylation agent capable of alkylating or alkenylating primary or secondary amino groups.

For example, this can be effected by contacting Compound (I') with a lower alkyl iodide or lower alkenyl iodide, preferably in an inert organic solvent and preferably in the presence of a scavenger base. Typically, this process is conducted at temperatures in the range of about from 0° to 100° C., preferably 20° to 45° C. for about from 1.0 to 72.0, preferably 2.0 to 18.0 hours. Where it is desired to alkylate or alkenylate only at $R^6$, then typically about from 1.0 to 1.1 moles of $R^6I$ reactant is used per mole of Compound (I'). Where it is desired to alkylate both amino hydrogens, then typically about from 1.9 to 4.0 moles of $R^6I$ are used per mole of Compound (I'). Also variation in $R^6$ and $R^7$ can be effected by first alkylation of only one of the two amino hydrogens and then alkylating the second amino hydrogen with an alkylating agent having a different $R^6$ alkyl or alkenyl group. Suitable inert organic solvents which can be used, include, for example, liquid halogenated alkanes; for example, methylene chloride, carbon tetrachloride, dichloroethane; tetrahydrofuran and the like. Suitable scavenger bases include, for example, the bases described hereinabove with respect to the reaction of Compound (A) with Compound (B).

The compounds of Formula (I'') wherein $R^6$ is lower alkyl (e.g., methyl) and $R^7$ is hydrogen or lower alkyl, can be advantageously prepared using dialkyl sulfate as the alkylating agent. This can be conveniently effected by contacting the compound of Formula (I') or (I'') with the desired lower alkyl sulfates in the presence of a strong base and preferably in an inert organic solvent in the presence of a phase transfer agent. Typically, this process is conducted at temperatures in the range of about from 0° to 100° C., preferably 20° to 45° C., using about from 1.0 to 4.0 moles of dialkyl sulfate per mole of Compound (I'). An excess, typically about 2.5 mole of base is used. Preferably, this process is also conducted in an inert organic solvent such as, for example, methylene chloride, carbon tetrachloride, dichloroethane, tetrahydrofuran, and the like.

Suitable strong bases which can be used include, for example, sodium hydroxide, potassium hydroxide, sodium ethoxide, sodium carbonate, potassium carbonate, and the like. Suitable phase transfer agents are agents which transfer hydrophilic ions into a lipophilic organic medium and include, for example, benzyl triethylammonium chloride, tetra-n-butylammonium chloride, methyltrioctylammonium chloride, and the like.

The compatible salts of Formula (I) can be prepared by conventional procedures by treating the compound of Formula (I) wherein $R^1$ and/or $R^2$ is hydrogen with a suitable strong base such as, for example, n-butyllithium, sodium hydride, potassium hydride, and the like, having the desired cation, by conventional procedures to replace an amine hydrogen with the desired carbon. The three-position enolate salts can be prepared via further treatment of the amine salt with base. Additional variations in the salt cation can also be effected via ion exchange with an ion exchange resin having the desired cation.

General Process Conditions

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary:

The term "lower alkyl" refers to both straight- and branched-chain alkyl groups having a total of from 1 through 6, preferably 1 through 4, carbon atoms and includes primary, secondary and tertiary alkyl groups.

Typical lower alkyls include, for example, methyl, ethyl, n-propyl, isopropyl, n-butyl, t-butyl.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "halo" refers to the group of fluoro, chloro, bromo or iodo.

The term "aryl" refers to aryl groups having 6 through 10 carbon atoms and includes, for example, phenyl, naphthyl, indenyl, and the like.

The term "substituted aryl" refers to aryl groups having 1 through 3 substituents independently selected from the group of lower alkyl, lower alkoxy, halonitro, or haloalkyl having 1 through 3 carbon atoms and 1 through 3 halo atoms. Typical substitued aryl groups include, for example, 2-fluorophenyl, 2-chlorophenyl, 2,6-dimethylphenyl, 4-fluorophenyl, 2-methylphenyl, 2-chloro,4-chloromethylphenyl, 2-nitro,5-methylphenyl, 2,4-dichlorophenyl, 3-trifluoromethylphenyl, 2-methoxyphenyl, and the like.

The term "arylalkylene" or "arylalkyl" refers to the group $ArR^5$- wherein Ar is aryl and $R^5$ is alkylene having 1 through 3 carbon atoms and includes both straight-chained and branched-chain alkylenes, for example, methylene, ethyl, 1-methylethyl, and propyl.

The term "(substituted aryl)alkylene" or "ring-substituted arylalkylene" refers to the group $Ar'R^5$- wherein $Ar'$ is substituted aryl and $R^5$ is alkylene as defined with respect to arylalkylene.

The term "compatible salts" refers to salts which do not significantly alter the herbicidal properties of the parent compound. Suitable salts include cation salts such as, for example, the cation replacement salts of lithium, sodium, potassium, alkali earth metals, ammonia, quaternary ammonium salts, and the like.

The term "room temperature" or "ambient temperature" refers to about 20°–25° C.

Utility

The compounds of Formula (I) exhibit both pre-emergence and post-emergence herbicidal activity and exhibit especially good pre-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary, examples are repeated to provide additional starting material for subsequent examples.

EXAMPLES

Example 1

Thien-2-yl-hydroxyacetonitrile

In this example 25.0 g of 2-formylthiophene was added to a stirred solution containing 10.93 g of sodium cyanide in 37 ml of water at room temperature. 63 ml of aqueous saturated sodium acid sulfite was then slowly added to the stirred mixture. During the addition of the sodium acid sulfite solution, small amounts (about 20 g) of ice were periodically added. The mixture was then stirred for another 15 minutes and extracted with ethyl ether. The ethyl ether extracts were combined, dried over magnesium sulfate and evaporated under vacuum affording 18.4 g of the title compound.

Example 2

Methyl Thien-2-yl-hydroxyacetate (a) In this example 6.8 g of methanol was added to a stirred solution of 26.9 g of thienyl-2-yl-hydroxyacetonitrile in 100 ml ethyl ether at about 10° C. Hydrogen chloride was then bubbled through this mixture until the formation of a salt precipitate was observed. The mixture was then stirred for about 15 minutes at about 10° C. and then filtered. The filter cake was washed with ethyl ether and then evaporated affording 18.2 g of the chloride salt of 2-(2-imino-2-methoxy-1-hydroxyethyl)thiophene.

(b) The above salt was then dissolved in water and stirred at room temperature for about 30 minutes and then extracted three times with ethyl ether.

The ethyl ether extracts were combined, dried over magnesium sulfate and concentrated by evaporation under vacuum, affording 8.3 g of the title compound.

The filtrate from step (a) was allowed to stand overnight (about 16–18 hours) at room temperature and was then filtered. The filter cake was treated as before affording an additional 11.7 g of chloride salt. This salt was then hydrolyzed with water as described above affording an additional 4.4 g of the title compound.

Similarly, by applying the procedures of Examples 1 and 2 using the appropriate heterocyclichydroxyacetonitrile starting materials in Example 1, the following compounds can be prepared.
Methyl thien-3-yl-hydroxyacetate;
Methyl(2,3-dihydrothien-2-yl)-hydroxyacetate;
Methyl tetrahydrothien-3-yl-hydroxyacetate;
Methyl(2H-thiopyran-2-yl)-hydroxyacetate;
Methyl fur-2-yl-hydroxyacetate;
Methyl fur-3-yl-hydroxyacetate;
Methyl(2,3-dihydrofur-2-yl)-hydroxyacetate;
Methyl tetrahydrofur-3-yl-hydroxyacetate;
Methyl(4H-pyran-2-yl)-hydroxyacetate;
Methyl(2H-3,4-dihydropyran-3-yl)-hydroxyacetate; and
Methyl(tetrahydropyran-2-yl)-hydroxyacetate.

Example 3

2-Thien-2-yl-3-oxo-4-(3-trifluoromethylphenyl)-5-amino-2,3-dihydrofuran

A dry, 250-ml, three-neck, round-bottom flask equipped with a mechanical stirrer, addition funnel and a reflux condenser bearing a nitrogen inlet tube was charged with 4.2 g of sodium and 100 ml of absolute ethanol. To the resulting sodium ethoxide solution was added dropwise a mixture of 21.1 g of methyl thien-2-yl-hydroxyacetate and 22.7 g of m-trifluoromethylphenyl-acetonitrile in 20 ml of ethanol. The resulting mixture was heated at reflux for 4–5 hours after which time it was added to 300–400 ml of water and extracted with petroleum ether. The aqueous phase was acidified with aqueous 10 weight percent hydrochloric acid and extracted two times with diethyl ether. The ether extracts were washed twice with saturated aqueous sodium bicarbonate, dried over magnesium sulfate and concentrated in vacuo to yield a thick dark oil. This oil was triturated with 20–30% ether/petroleum ether which afforded 4.9 g of the title compound as a tan powder.

Similarly, by applying the above-described procedure using the appropriate (substituted phenyl) acetonitrile starting materials the following compounds can also be prepared:

2-(thien-2-yl)-3-oxo-4-(5-chloro-3-trifluoromethyl-phenyl)-5-amino-2,3-dihydrofuran;
2-(thien-2-yl)-3-oxo-4-(4-chloro-3-trifluoromethyl-phenyl)-5-amino-2,3-dihydrofuran;
2-(thien-2-yl)-3-oxo-4-(2-bromo-3-trifluoromethyl-phenyl)-5-amino-2,3-dihydrofuran;
2-(thien-2-yl)-3-oxo-4-(6-fluoro-3-trifluoromethyl-phenyl)-5-amino-2,3-dihydrofuran;
2-(thien-2-yl)-3-oxo-4-(4-methyl-3-trifluoromethyl-phenyl)-5-amino-2,3-dihydrofuran;
2-(thien-2-yl)-3-oxo-4-(5-methoxy-3-trifluoromethyl-phenyl)-5-amino-2,3-dihydrofuran;
2-(thien-2-yl)-3-oxo-4-(6-isopropyl-3-trifluoromethyl-phenyl)-5-amino-2,3-dihydrofuran;
2-(thien-2-yl)-3-oxo-4-(3,5-di-trifluoromethylphenyl)-5-amino-2,3-dihydrofuran;
2-(thien-2-yl)-3-oxo-4-(3-propylphenyl)-5-amino-2,3-dihydrofuran;
2-(thien-2-yl)-3-oxo-4-(3-methylphenyl)-5-amino-2,3-dihydrofuran;
2-(thien-2-yl)-3-oxo-4-(3-fluorophenyl)-5-amino-2,3-dihydrofuran;
2-(thien-2-yl)-3-oxo-4-(3-methoxyphenyl)-5-amino-2,3-dihydrofuran;
2-(thien-2-yl)-3-oxo-4-(3-iodophenyl)-5-amino-2,3-dihydrofuran; and
2-(thien-2-yl)-3-oxo-4-(2-chloro-3-methylphenyl)-5-amino-2,3-dihydrofuran;
2-(thien-2-yl)-3-oxo-4-(4-ethyl-3-methylphenyl)-5-amino-2,3-dihydrofuran;
2-(thien-2-yl)-3-oxo-4-(5-methoxy-3-chlorophenyl)-5-amino-2,3-dihydrofuran;
2-(thien-2-yl)-3-oxo-4-(6-ethoxy-3-chlorophenyl)-5-amino-2,3-dihydrofuran;
2-(thien-2-yl)-3-oxo-4-(3,5-diethoxyphenyl)-5-amino-2,3-dihydrofuran;
2-(thien-2-yl)-3-oxo-4-(3-bromophenyl)-5-amino-2,3-dihydrofuran;
2-(thien-2-yl)-3-oxo-4-(3-chloro-4-methylphenyl)-5-amino-2,3-dihydrofuran;
2-(thien-2-yl)-3-oxo-4-(3-bromo-2-ethylphenyl)-5-amino-2,3-dihydrofuran;
2-(thien-2-yl)-3-oxo-4-(3,6-dimethylphenyl)-5-amino-2,3-dihydrofuran;
2-(thien-2-yl)-3-oxo-4-(3-iodo-4-methylphenyl)-5-amino-2,3-dihydrofuran;
2-(thien-2-yl)-3-oxo-4-(3-chlorophenyl)-5-amino-2,3-dihydrofuran;
2-(thien-2-yl)-3-oxo-4-(3-butylphenyl)-5-amino-2,3-dihydrofuran;
2-(thien-2-yl)-3-oxo-4-(3-butoxyphenyl)-5-amino-2,3-dihydrofuran; and
2-(thien-2-yl)-3-oxo-4-(3-isopropoxyphenyl)-5-amino-2,3-dihydrofuran.

Similarly by applying the above procedure using the appropriate (substituted phenyl)acetonitrile and the appropriate methyl heterocycle-hydroxyacetate compound of the list given in Example 2 the corresponding 2-heterocycle analogs of the above compounds can also be prepared for example:

2-(thien-3-yl)-3-oxo-4-(3-bromophenyl)-5-amino-2,3-dihydrofuran;
2-(thien-3-yl)-3-oxo-4-(3-iodophenyl)-5-amino-2,3-dihydrofuran;
2-(thien-3-yl)-3-oxo-4-(3-propylphenyl)-5-amino-2,3-dihydrofuran;
2-(thien-3-yl)-3-oxo-4-(3-methoxyphenyl)-5-amino-2,3-dihydrofuran;
2-(thien-3-yl)-3-oxo-4-(3-fluorophenyl)-5-amino-2,3-dihydrofuran; and
2-(thien-3-yl)-3-oxo-4-(3-propoxyphenyl)-5-amino-2,3-dihydrofuran.
2-(thien-3-yl)-3-oxo-4-(3-trifluoromethylphenyl)-5-amino-2,3-dihydrofuran;
2-(thien-3-yl)-3-oxo-4-(3-chlorophenyl)-5-amino-2,3-dihydrofuran;
2-(2,3-dihydrothien-2-yl)-3-oxo-4-(3-trifluoromethyl-phenyl)-5-amino-2,3-dihydrofuran;
2-(2,3-dihydrothien-2-yl)-3-oxo-4-(3,5-diethoxyphenyl)-5-amino-2,3-dihydrofuran;
2-(tetrahydrothien-3-yl)-3-oxo-4-(3-trifluoromethyl-phenyl)-5-amino-2,3-dihydrofuran;
2-(2H-thiopyran-2-yl)-3-oxo-4-(3-bromophenyl)-5-amino-2,3-dihydrofuran;
2-(2H-thiopyran-2-yl)-3-oxo-4-(2-chloro-3-trifluoromethylphenyl)-5-amino-2,3-dihydrofuran;
2-(fur-2-yl)-3-oxo-4-(3-trifluoromethyl-5-chloro-phenyl)-5-amino-2,3-dihydrofuran;
2-(fur-2-yl)-3-oxo-4-(3-fluorophenyl)-5-amino-2,3-dihydrofuran;
2-(fur-2-yl)-3-oxo-4-(3-bromophenyl)-5-amino-2,3-dihydrofuran;
2-(fur-2-yl)-3-oxo-4-(3-chlorophenyl)-5-amino-2,3-dihydrofuran;
2-(fur-2-yl)-3-oxo-4-(3-methylphenyl)-5-amino-2,3-dihydrofuran;
2-(fur-2-yl)-3-oxo-4-(2-butoxy-3-trifluoromethyl-phenyl)-5-amino-2,3-dihydrofuran;
2-(fur-2-yl)-3-oxo-4-(3-trifluoromethylphenyl)-5-amino-2,3-dihydrofuran;
2-(fur-2-yl)-3-oxo-4-(3-iodophenyl)-5-amino-2,3-dihydrofuran;
2-(fur-2-yl)-3-oxo-4-(3-propylphenyl)-5-amino-2,3-dihydrofuran;
2-(2,3-dihydrofur-2-yl)-3-oxo-4-(3-trifluoromethyl-phenyl)-5-amino-2,3-dihydrofuran;
2-(2,3-dihydrofur-2-yl)-3-oxo-4-(2-bromo-3-trifluoromethylphenyl)-5-amino-2,3-dihydrofuran;

2-(tetrahydrofur-2-yl)-3-oxo-4-(3-trifluoromethyl-
phenyl)-5-amino-2,3-dihydrofuran;
2-(tetrahydrofur-2-yl)-3-oxo-4-(4-methyl-3-trifluorome-
thylphenyl)-5-amino-2,3-dihydrofuran;
2-(fur-3-yl)-3-oxo-4-(5-chloro-3-trifluoromethyl-
phenyl)-5-amino-2,3-dihydrofuran;
2-(fur-3-yl)-3-oxo-4-(3-fluorophenyl)-5-amino-2,3-dihy-
drofuran;
2-(fur-3-yl)-3-oxo-4-(3-bromophenyl)-5-amino-2,3-dihy-
drofuran;
2-(fur-3-yl)-3-oxo-4-(3-chlorophenyl)-5-amino-2,3-dihy-
drofuran;
2-(fur-3-yl)-3-oxo-4-(3-methylphenyl)-5-amino-2,3-
dihydrofuran;
2-(fur-3-yl)-3-oxo-4-(2-butoxy-3-trifluoromethyl-
phenyl)-5-amino-2,3-dihydrofuran;
2-(fur-3-yl)-3-oxo-4-(3-trifluoromethylphenyl)-5-amino-
2,3-dihydrofuran;
2-(fur-3-yl)-3-oxo-4-(3-methoxyphenyl)-5-amino-2,3-
dihydrofuran;
2-(fur-3-yl)-3-oxo-4-(3-ethylphenyl)-5-amino-2,3-dihy-
drofuran;
2-(2,3-dihydrofur-2-yl)-3-oxo-4-(3-trifluoromethyl-
phenyl)-5-amino-2,3-dihydrofuran;
2-(2,3-dihydrofur-2-yl)-3-oxo-4-(2-bromo-3-tri-
fluoromethylphenyl)-5-amino-2,3-dihydrofuran;
2-(tetrahydrofur-3-yl)-3-oxo-4-(3-trifluoromethyl-
phenyl)-5-amino-2,3-dihydrofuran;
2-(tetrahydrofur-3-yl)-3-oxo-4-(4-methyl-3-trifluorome-
thylphenyl)-5-amino-2,3-dihydrofuran;
2-(4H-pyran-2-yl)-3-oxo-4-(3-trifluoromethylphenyl)-5-
amino-2,3-dihydrofuran;
2-(4H-pyran-2-yl)-3-oxo-4-(3-fluorophenyl)-5-amino-
2,3-dihydrofuran;
2-(4H-pyran-2-yl)-3-oxo-4-(3-methylphenyl)-5-amino-
2,3-dihydrofuran;
2-(4H-pyran-2-yl)-3-oxo-4-(2-methyl-3-trifluoromethyl-
phenyl)-5-amino-2,3-dihydrofuran;
2-(4H-pyran-2-yl)-3-oxo-4-(2-nitro-3-methylphenyl)-5-
amino-2,3-dihydrofuran;
2-(2H-3,4-dihydropyran-3-yl)-3-oxo-4-(3-trifluorome-
thylphenyl)-5-amino-2,3-dihydrofuran;
2-(2H-3,4-dihydropyran-3-yl)-3-oxo-4-(2-chloro-3-tri-
fluoromethylphenyl)-5-amino-2,3-dihydrofuran;
2-(-2H-3,4-dihydropyran-4-yl)-3-oxo-4-(3-fluoro-
phenyl)-5-amino-2,3-dihydrofuran;
2-(2H-3,4-dihydropyran-3-yl)-3-oxo-4-(2-chloro-3-
methylphenyl)-5-amino-2,3-dihydrofuran;
2-(tetrahydropyran-2-yl)-3-oxo-4-(3-trifluoromethyl-
phenyl)-5-amino-2,3-dihydrofuran;
2-tetrahydropyran-2-yl-3-oxo-4-(3-chloro-5-methyl-
phenyl)-5-amino-2,3-dihydrofuran;
2-(tetrahydropyran-2-yl)-3-oxo-4-(3-fluorophenyl)-5-
amino-2,3-dihydrofuran; and
2-(tetrahydropyran-2-yl)-3-oxo-4-(3-ethylphenyl)-5-
amino-2,3-dihydrofuran.

Example 4

2-Thien-2-yl-3-oxo-4-(-3-trifluoromethylphenyl)-5-
methylamino-2,3-dihydrofuran

In this example about 0.36 g of solid sodium hydrox-
ide was dissolved in a small amount of water and then
added to 100 ml of methylene chloride containing 1.4 g
of 2-thien-2-yl-3-oxo-4-(3-trifluoromethylphenyl)-5-
amino-2,3-dihydrofuran. 0.20 g of benzyltriethylam-
monium chloride was added and then a mixture contain-
ing 0.84 ml of dimethyl sulfate in about 5.0 ml of methy-
lene chloride was slowly added at room temperature.
The mixture was stirred at room temperature for about
one hour and then washed twice with water, twice with
1N. aqueous hydrochloric acid, twice with sodium bi-
carbonate, dried over magnesium sulfate and then con-
centrated by evaporation under vacuum. The residue
was then triturated in a mixture of ethyl ether and petro-
leum ether affording 1.4 g of the title compound.

Similarly, by following the same procedure using the
products listed in Example 3 as starting materials, the
corresponding 5-methylamino homologs thereof can be
prepared, for example:
2-(thien-2-yl)-3-oxo-4-(5-chloro-3-trifluoromethyl-
phenyl)-5-methylamino-2,3-dihydrofuran;
2-(thien-2-yl)-3-oxo-4-(4-chloro-3-trifluoromethyl-
phenyl)-5-methylamino-2,3-dihydrofuran;
2-(thien-2-yl)-3-oxo-4-(2-bromo-3-trifluoromethyl-
phenyl)-5-methylamino-2,3-dihydrofuran;
2-(thien-2-yl)-3-oxo-4-(6-fluoro-3-trifluoromethyl-
phenyl)-5-methylamino-2,3-dihydrofuran;
2-(thien-2-yl)-3-oxo-4-(4-methyl-3-trifluoromethyl-
phenyl)-5-methylamino-2,3-dihydrofuran;
2-(thien-2-yl)-3-oxo-4-(5-methoxy-3-trifluoromethyl-
phenyl)-5-methylamino-2,3-dihydrofuran;
2-(thien-2-yl)-3-oxo-4-(6-isopropyl-3-trifluoromethyl-
phenyl)-5-methylamino-2,3-dihydrofuran;
2-(thien-2-yl)-3-oxo-4-(3,5-di-trifluoromethylphenyl)-5-
methylamino-2,3-dihydrofuran;
2-(thien-2-yl)-3-oxo-4-(3-propylphenyl)-5-
methylamino-2,3-dihydrofuran;
2-(thien-2-yl)-3-oxo-4-(3-methylphenyl)-5-
methylamino-2,3-dihydrofuran;
2-(thien-2-yl)-3-oxo-4-(3-fluorophenyl)-5-methylamino-
2,3-dihydrofuran;
2-(thien-2-yl)-3-oxo-4-(3-methoxyphenyl)-5-
methylamino-2,3-dihydrofuran;
2-(thien-2-yl)-3-oxo-4-(3-iodophenyl)-5-methylamino-
2,3-dihydrofuran; and
2-(thien-2-yl)-3-oxo-4-(2-chloro-3-methylphenyl)-5-
methylamino-2,3-dihydrofuran;
2-(thien-2-yl)-3-oxo-4-(4-ethyl-3-methylphenyl)-5-
methylamino-2,3-dihydrofuran;
2-(thien-2-yl)-3-oxo-4-(5-methoxy-3-chlorophenyl)-5-
methylamino-2,3-dihydrofuran;
2-(thien-2-yl)-3-oxo-4-(6-ethoxy-3-chlorophenyl)-5-
methylamino-2,3-dihydrofuran;
2-(thien-2-yl)-3-oxo-4-(3,5-diethoxyphenyl)-5-
methylamino-2,3-dihydrofuran;
2-(thien-2-yl)-3-oxo-4-(3-bromophenyl)-5-methylamino-
2,3-dihydrofuran;
2-(thien-2-yl)-3-oxo-4-(3-chloro-4-methylphenyl)-5-
methylamino-2,3-dihydrofuran;
2-(thien-2-yl)-3-oxo-4-(3-bromo-2-ethylphenyl)-5-
methylamino-2,3-dihydrofuran;
2-(thien-2-yl)-3-oxo-4-(3,6-dimethylphenyl)-5-
methylamino-2,3-dihydrofuran;
2-(thien-2-yl)-3-oxo-4-(3-iodo-4-methylphenyl)-5-
methylamino-2,3-dihydrofuran;
2-(thien-2-yl)-3-oxo-4-(3-chlorophenyl)-5-methylamino-
2,3-dihydrofuran;
2-(thien-2-yl)-3-oxo-4-(3-butylphenyl)-5-methylamino-
2,3-dihydrofuran;
2-(thien-2-yl)-3-oxo-4-(3-butoxyphenyl)-5-
methylamino-2,3-dihydrofuran;
2-(thien-2-yl)-3-oxo-4-(3-isopropoxyphenyl)-5-
methylamino-2,3-dihydrofuran;
2-(thien-3-yl)-3-oxo-4-(3-bromophenyl)-5-methylamino-
2,3-dihydrofuran;

2-(thien-3-yl)-3-oxo-4-(3-iodophenyl)-5-methylamino-2,3-dihydrofuran;
2-(thien-3-yl)-3-oxo-4-(2-methylphenyl)-5-methylamino-2,3-dihydrofuran;
2-(thien-3-yl)-3-oxo-4-(3-methoxyphenyl)-5-methylamino-2,3-dihydrofuran;
2-(thien-3-yl)-3-oxo-4-(3-fluorophenyl)-5-methylamino-2,3-dihydrofuran;
2-(thien-3-yl)-3-oxo-4-(3-propoxyphenyl)-5-methylamino-2,3-dihydrofuran;
2-(thien-3-yl)-3-oxo-4-(3-trifluoromethylphenyl)-5-methylamino-2,3-dihydrofuran;
2-(thien-3-yl)-3-oxo-4-(3-chlorophenyl)-5-methylamino-2,3-dihydrofuran;
2-(2,3-dihydrothien-2-yl)-3-oxo-4-(3-trifluoromethylphenyl)-5-methylamino-2,3-dihydrofuran;
2-(2,3-dihydrothien-2-yl)-3-oxo-4-(3,5-diethoxyphenyl)-5-methylamino-2,3-dihydrofuran;
2-(tetrahydrothien-3-yl)-3-oxo-4-(3-trifluoromethylphenyl)-5-methylamino-2,3-dihydrofuran;
2-(2H-thiopyran-2-yl)-3-oxo-4-(3-bromophenyl)-5-methylamino-2,3-dihydrofuran;
2-(2H-thiopyran-2-yl)-3-oxo-4-(2-chloro-3-trifluoromethylphenyl)-5-methylamino-2,3-dihydrofuran;
2-(fur-2-yl)-3-oxo-4-(5-chloro-3-trifluoromethylphenyl)-5-methylamino-2,3-dihydrofuran;
2-(fur-2-yl)-3-oxo-4-(3-fluorophenyl)-5-methylamino-2,3-dihydrofuran;
2-(fur-2-yl)-3-oxo-4-(3-bromophenyl)-5-methylamino-2,3-dihydrofuran;
2-(fur-2-yl)-3-oxo-4-(3-chlorophenyl)-5-methylamino-2,3-dihydrofuran;
2-(fur-2-yl)-3-oxo-4-(3-methylphenyl)-5-methylamino-2,3-dihydrofuran;
2-(fur-2-yl)-3-oxo-4-(2-butoxy-3-trifluoromethylphenyl)-5-methylamino-2,3-dihydrofuran;
2-(fur-2-yl)-3-oxo-4-(3-trifluoromethylphenyl)-5-methylamino-2,3-dihydrofuran;
2-(fur-2-yl)-3-oxo-4-(3-iodophenyl)-5-methylamino-2,3-dihydrofuran;
2-(fur-2-yl)-3-oxo-4-(3-propylphenyl)-5-methylamino-2,3-dihydrofuran;
2-(2,3-dihydrofur-2-yl)-3-oxo-4-(3-trifluoromethylphenyl)-5-methylamino-2,3-dihydrofuran;
2-(2,3-dihydrofur-2-yl)-3-oxo-4-(2-bromo-3-trifluoromethylphenyl)-5-methylamino-2,3-dihydrofuran;
2-(tetrahydrofur-2-yl)-3-oxo-4-(3-trifluoromethylphenyl)-5-methylamino-2,3-dihydrofuran;
2-(tetrahydrofur-2-yl)-3-oxo-4-(4-methyl-3-trifluoromethylphenyl)-5-methylamino-2,3-dihydrofuran;
2-(fur-3-yl)-3-oxo-4-(5-chloro-3-trifluoromethylphenyl)-5-methylamino-2,3-dihydrofuran;
2-(fur-3-yl)-3-oxo-4-(3-fluorophenyl)-5-methylamino-2,3-dihydrofuran;
2-(fur-3-yl)-3-oxo-4-(3-bromophenyl)-5-methylamino-2,3-dihydrofuran;
2-(fur-3-yl)-3-oxo-4-(3-chlorophenyl)-5-methylamino-2,3-dihydrofuran;
2-(fur-3-yl)-3-oxo-4-(3-methylphenyl)-5-methylamino-2,3-dihydrofuran;
2-(fur-3-yl)-3-oxo-4-(2-butoxy-3-trifluoromethylphenyl)-5-methylamino-2,3-dihydrofuran;
2-(fur-3-yl)-3-oxo-4-(3-trifluoromethylphenyl)-5-methylamino-2,3-dihydrofuran;
2-(fur-3-yl)-3-oxo-4-(3-methoxyphenyl)-5-methylamino-2,3-dihydrofuran;
2-(fur-3-yl)-3-oxo-4-(3-ethylphenyl)-5-methylamino-2,3-dihydrofuran;
2-(2,3-dihydrofur-2-yl)-3-oxo-4-(3-trifluoromethylphenyl)-5-methylamino-2,3-dihydrofuran;
2-(2,3-dihydrofur-2-yl)-3-oxo-4-(2-bromo-3-trifluoromethylphenyl)-5-methylamino-2,3-dihydrofuran;
2-(tetrahydrofur-3-yl)-3-oxo-4-(3-trifluoromethylphenyl)-5-methylamino-2,3-dihydrofuran;
2-(tetrahydrofur-3-yl)-3-oxo-4-(4-methyl-b 3-trifluoromethylphenyl)-5-methylamino-2,3-dihydrofuran;
2-(4H-pyran-2-yl)-3-oxo-4-(3-trifluoromethylphenyl)-5-methylamino-2,3-dihydrofuran;
2-(4H-pyran-2-yl)-3-oxo-4-(3-fluorophenyl)-5-methylamino-2,3-dihydrofuran;
2-(4H-pyran-2-yl)-3-oxo-4-(3-methylphenyl)-5-methylamino-2,3-dihydrofuran;
2-(4H-pyran-2-yl)-3-oxo-4-(2-methyl-3-trifluoromethylphenyl)-5-methylamino-2,3-dihydrofuran;
2-(4H-pyran-2-yl)-3-oxo-4-(2-nitro-3-methylphenyl)-5-methylamino-2,3-dihydrofuran;
2-(2H-3,4-dihydropyran-3-yl)-3-oxo-4-(3-trifluoromethylphenyl)-5-methylamino-2,3-dihydrofuran;
2-(2H-3,4-dihydropyran-3-yl)-3-oxo-4-(2-chloro-3-trifluoromethylphenyl)-5-methylamino-2,3-dihydrofuran;
2-(2H-3,4-dihydropyran-3-yl)-3-oxo-4-(3-fluorophenyl)-5-methylamino-2,3-dihydrofuran;
2-(2H-3,4-dihydropyran-4-yl)-3-oxo-4(3-methylphenyl)-5-methylamino-2,3-dihydrofuran;
2-(tetrahydropyran-2-yl)-3-oxo-4-(3-trifluoromethylphenyl)-5-methylamino-2,3-dihydrofuran;
2-(tetrahydropyran-2-yl)-3-oxo-4-(3-chloro-5-methylphenyl)-5-methylamino-2,3-dihydrofuran;
2-(tetrahydropyran-3-yl)-3-oxo-4-(3-fluorophenyl)-5-methylamino-2,3-dihydrofuran; and
2-(tetrahydropyran-4-yl)-3-oxo-4-(3-ethylphenyl)-5-methylamino-2,3-dihydrofuran.

Example 5

2-(Thien-2-yl)-3-oxo-4-(3-trifluoromethylphenyl)-5-allylamino-2,3-dihydrofuran

This example illustrates a preparation which can be used to prepare the 5-allylamino substituted compounds of the invention.

One gram of sodium hydroxide in 4.0 ml of water is added to a mixture of 1 mmol of 2-(thien-2-yl)-3-oxo-4-(3-trifluoromethylphenyl)-5-amino-2,3-dihydrofuran in 80 ml of methylene chloride at room temperature followed by the addition of 1 mmol of allyl bromide and 0.27 g of benzyltriethylammonium chloride. The resulting mixture is stirred at room temperature for about 18 hours after which time it can be washed three times with water, dried over magnesium sulfate and concentrated in vacuo. The residue can be purified by chromatography over silica gel to yield the title compound.

Similarly, by applying this procedure to the products listed in Examples 3 and 4, the corresponding 5-allylamino analogs thereof can be prepared. Similarly, by approximately doubling the amount of allyl bromide and sodium hydroxide, the corresponding 5-diallylamino analogs thereof can be prepared.

In a like manner, by using ethyl bromide in place of allyl bromide, the corresponding 5-ethyl and 5-diethyl analogs can be prepared.

Similarly, by using the 5-methylamino analogs of Example 4 as starting materials, the corresponding 5-N-methyl-N-allylamino and 5-N-methyl-N-ethyl analogs can be prepared.

Example 6

Lithium salt of 2-thien-2-yl-3-oxo-4-(3-trifluoromethylphenyl)-5-methylamino-2,3-dihydrofuran ($R^1$=—$CH_3$, $R^2$=Li)

This example illustrates a preparation which can be used to prepare the lithium salts of the invention.

In this example, 5.4 ml of 1.6M n-butyllithium in hexane is added dropwise to a stirred solution containing 2.81 g of 2-thien-2-yl-3-oxo-4-(3-trifluoromethylphenyl)-5-amino-2,3-dihydrofuran in 25 ml of tetrahydrofuran at −30° C. The mixture is stirred for 20 minutes and can then be concentrated by evaporation in vacuo to yield the title compound.

Similarly, by following the same procedure, the corresponding lithium salts of the compounds of Examples 3–5 can be prepared.

Example 7

The compounds listed in Table A hereinbelow were prepared using the appropriate starting materials and procedures described in the Examples hereinabove.

Seeds of the test vegetation were planted in a pot of soil and the test solution was sprayed uniformly onto the soil surface either at a dose of 27.5 micrograms/cm². The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm². After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound

TABLE A

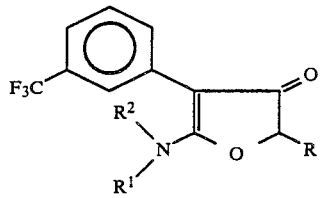

| | | | | ELEMENTAL ANALYSIS | | | | | Melting |
| | | | | Carbon | | Hydrogen | | Nitrogen | Point |
| No. | $R^1$ | $R^2$ | R | Calc. | Found | Calc. | Found | Calc. | Found | °C. |
|---|---|---|---|---|---|---|---|---|---|---|
| 1 | H | H | thien-2-yl | 55.38 | 54.92 | 3.08 | 2.94 | 4.31 | 4.34 | 198–199* |
| 2 | $CH_3$ | H | thien-2-yl | 56.64 | 56.22 | 3.54 | 3.78 | 4.13 | 4.14 | 141–144* |
| 3 | H | H | thien-3-yl | 55.38 | 55.89 | 3.08 | 3.39 | 4.31 | 4.32 | 143–144 |
| 4 | $CH_3$ | H | thien-3-yl | 56.64 | 56.63 | 3.54 | 3.79 | 4.13 | 4.2 | 135–138 |
| 5 | $CH_2CH_3$ | H | thien-3-yl | 57.79 | 58.35 | 3.97 | 4.19 | 3.97 | 3.74 | 135–138 |

*Decomposition

Example 8

In this example, the compounds of Table A were respectively tested using the procedures described hereinbelow for pre-emergent and post-emergent activity against a variety of grasses and broad-leaf plants including one grain crop and one broad-leaf crop. The compounds tested are identified by compound number in Table A hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

was rated based on these observations. A 0-to-100 scale was used, 0 representing no phytotoxicity, 100 representing complete kill. The results of these tests are summarized in Table 2.

TABLE 1

| | Pre-Emergence Herbicidal Activity Application Rate: 27.5 micrograms/cm², unless otherwise noted | | | | | | | |
|---|---|---|---|---|---|---|---|---|
| | Broad-Leaf Plants % Phytotoxicity | | | | Grasses % Phytotoxicity | | | |
| Compound No. | Lambs-quarter | Mustard | Pig weed | Soy bean | Crab grass | Water grass | Wild Oats | Rice |
| 1 | 100 | 100 | 100 | 100 | 100 | 100 | 99 | 97 |
| 2 | 100 | 100 | 100 | 100 | 100 | 100 | 100 | 99 |
| 3 | 100 | 100 | 100 | 90 | 100 | 100 | 100 | 100 |
| 4 | 100 | 100 | 100 | 100 | 100 | 100 | 100 | 100 |
| 5 | 100 | 100 | 100 | 95 | 100 | 100 | 100 | 98 |

TABLE 2

| | Post-Emergence Herbicidal Activity Application Rate: 27.5 micrograms/cm$^2$, unless otherwise noted | | | | | | | |
|---|---|---|---|---|---|---|---|---|
| | Broad-Leaf Plants % Phytotoxicity | | | | Grasses % Phytotoxicity | | | |
| Compound No. | Lambs-quarter | Mustard | Pig weed | Soy bean | Crab grass | Water grass | Wild Oats | Rice |
| 1 | 65 | 99 | 68 | 38 | 45 | 60 | 65 | 30 |
| 2 | 98 | 100 | 90 | 75 | 58 | 70 | 75 | 40 |
| 3 | 70 | 90 | 65 | 70 | 80 | 60 | 75 | 25 |
| 4 | Not Tested | — | — | — | — | — | — | — |
| 5 | 85 | 95 | 70 | 90 | 70 | 90 | 93 | 70 |

As can be seen from the above Table 1, the test compounds of the invention exhibited a broad spectrum of excellent pre-emergence phytotoxic activity. Moreover, as shown by Table 2 the compounds also exhibit a broad spectrum of post-emergence phytotoxic activity and especially so Compound No. 2.

Obviously, many modifications and variations of the invention described hereinabove and below can be made without departing from the essence and scope thereof.

What is claimed is:

1. A compound having the formula:

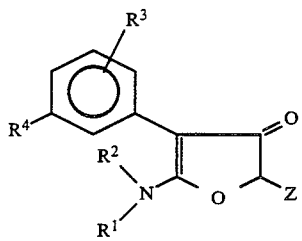

(I)

wherein
R$^1$ and R$^2$ are independently hydrogen, lower alkyl having 1 through 4 carbon atoms or alkenyl having 3 through 6 carbon atoms;
R$^3$ is hydrogen, lower alkyl, lower alkoxy, halo, or trifluoromethyl and can be at any available position on the phenyl ring;
R$^4$ is lower alkyl, lower alkoxy, halo, or trifluoromethyl;
Z is a saturated or unsaturated sulfur or oxygen heterocycle radical having 5 or 6 ring atoms one of which is sulfur or oxygen and the remainder of which are carbon atoms;
and compatible cation salts thereof.

2. The compound of claim 1 wherein R$^1$ and R$^2$ are independently selected from the group of hydrogen, methyl or ethyl and R$^3$ is hydrogen.

3. The compound of claim 2 wherein one of R$^1$ or R$^2$ is hydrogen and the other is hydrogen, methyl or ethyl.

4. The compound of claim 1 wherein R$^3$ is hydrogen.

5. The compound of claim 1 wherein Z is a wholly unsaturated heterocycle radical or a partially unsaturated heterocycle radical having a single double bond.

6. The compound of claim 1 wherein Z is a saturated heterocycle radical.

7. The compound of claim 1 wherein Z has the formula

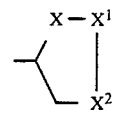

wherein one of X, X$^1$, and X$^2$ is sulfur or oxygen and the others are carbon atoms, and the dotted line indicates that the ring can be saturated, or can have 1 or 2 double bonds.

8. The compound of claim 1 wherein Z has the formula

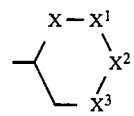

wherein one of X, X$^1$, X$^2$ and X$^3$ is oxygen or sulfur and the others are carbon atoms and the dotted line indicates the ring can be saturated or can have 1 or 2 double bonds.

9. The compound of claim 3 wherein Z is thienyl.
10. The compound of claim 3 wherein Z is furyl.
11. The compound of claim 3 wherein Z is thiopyranyl or pyranyl.
12. The compound of claim 1 wherein said compound is selected from the group having the formula:

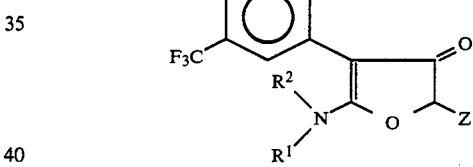

wherein R$^1$, R$^2$, R$^3$ and Z are as defined in claim 1; and compatible cation salts thereof.

13. The compound of claim 12 wherein R$^1$ and R$^2$ are independently hydrogen, methyl or ethyl and R$^3$ is hydrogen and compatible cation salts thereof.
14. The compound of claim 13 wherein one of R$^1$ or R$^2$ is hydrogen and the other is hydrogen, methyl or ethyl and compatible cation salts thereof.
15. The compound of claim 14 wherein Z is thienyl.
16. The compound of claim 14 wherein Z is furyl.
17. The compound of claim 14 wherein Z is dihydrothienyl or dihydrofuryl.
18. The compound of claim 14 wherein Z is tetrahydrothienyl or tetrahydrofuryl.
19. The compound of claim 14 wherein Z is thiopyranyl.
20. The compound of claim 14 wherein Z is pyranyl.
21. The compound of claim 14 wherein Z is dihydropyranyl or dihydrothiopyranyl.
22. The compound of claim 14 wherein Z is tetrahydropyranyl or dihydrothiopyranyl.
23. The compound of claim 14 wherein Z is thien-2-yl and one of R$^1$ or R$^2$ is hydrogen and the other is hydrogen, methyl or ethyl; and compatible salts thereof.
24. The compound of claim 23 wherein one of R$^1$ or R$^2$ is hydrogen and the other is methyl; and compatible salts thereof.

25. The compound of claim 13 wherein one of $R^1$ or $R^2$ is hydrogen and the other is ethyl; and compatible salts thereof.

26. The compound of claim 23 wherein $R^1$ and $R^2$ are each hydrogen; and compatible salts thereof.

27. The compound of claim 14 wherein Z is thien-3-yl; $R^3$ is hydrogen, and one of $R^1$ or $R^2$ is hydrogen and the other is methyl; and compatible salts thereof.

28. The compound of claim 14 wherein Z is fur-2-yl or fur-3-yl; $R^3$ is hydrogen and one of $R^1$ or $R^2$ is hydrogen and the other is methyl; and compatible salts thereof.

29. The compound of claim 12 wherein $R^3$ is hydrogen.

30. A herbicidal composition comprising a herbicidally effective amount of the compound of claim 1, or mixtures of such compounds, and a compatible carrier.

31. A herbicidal composition comprising a herbicidally effective amount of the compound of claim 23, or mixtures thereof, and a compatible carrier.

32. A method for preventing or destroying plants which comprises applying a herbicidally effective amount of the compound of claim 1, or mixtures thereof, to the foliage or potential growth medium of said plants.

33. A method for preventing or destroying plants which comprises applying a herbicidally effective amount of the compound of claim 23, or mixtures thereof, to the foliage or potential growth medium of said plants.

34. A plant growth regulating composition which comprises an amount of the compound of claim 1, or mixtures thereof, effective to alter the growth pattern of plants.

35. A method for regulating the growth of plants which comprises applying to the foliage of said plants or their growth medium an amount of the compound of claim 1, or mixtures thereof, effective to alter the growth pattern of such plants.

* * * * *

UNITED STATES PATENT AND TRADEMARK OFFICE
CERTIFICATE OF CORRECTION

PATENT NO. : 4,537,623
DATED : August 27, 1985
INVENTOR(S) : Carl E. Ward

It is certified that error appears in the above-identified patent and that said Letters Patent are hereby corrected as shown below:

Claim 8, Col. 18, Line 15, 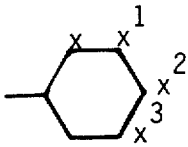 should appear as follows: 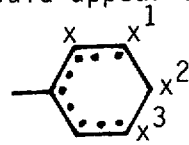

Claim 7, Col. 18, Line 1-7, 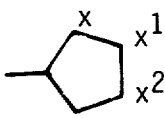 should appear as follows: 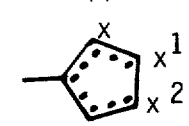

Claim 25, Col. 19, Line 1, "claim 13" should read --claim 23--.

Signed and Sealed this

Ninth Day of September 1986

[SEAL]

Attest:

DONALD J. QUIGG

Attesting Officer        Commissioner of Patents and Trademarks